United States Patent
Verlaan et al.

(10) Patent No.: US 7,288,570 B2
(45) Date of Patent: Oct. 30, 2007

(54) STIMULATION OF IN VIVO PRODUCTION OF PROTEINS

(75) Inventors: George Verlaan, Wageningen (NL); Rudolf Leonardus Lodewijk Smeets, Venlo (NL); Robert Reese Wolfe, League City, TX (US)

(73) Assignee: Nutricia N.V., Zoetermeer (NL)

( * ) Notice: Subject to any disclaimer, the term of this patent is extended or adjusted under 35 U.S.C. 154(b) by 338 days.

(21) Appl. No.: 10/325,711

(22) Filed: Dec. 20, 2002

(65) Prior Publication Data

US 2004/0122097 A1    Jun. 24, 2004

(51) Int. Cl.
*A01N 37/12* (2006.01)
(52) U.S. Cl. .................................................. 514/561
(58) Field of Classification Search ................. 514/561
See application file for complete search history.

(56) References Cited

U.S. PATENT DOCUMENTS

| | | | |
|---|---|---|---|
| 4,687,782 A | 8/1987 | Brantman | 514/561 |
| 5,242,697 A | 9/1993 | Luca | 426/231 |
| 5,639,731 A * | 6/1997 | Newsholme et al. | 514/23 |
| 5,817,329 A * | 10/1998 | Gardiner | 424/439 |
| 6,051,236 A * | 4/2000 | Portman | 424/725 |
| 6,221,418 B1 * | 4/2001 | Bergenfield et al. | 426/549 |
| 6,241,996 B1 * | 6/2001 | Hahn | 424/439 |
| 6,245,378 B1 | 6/2001 | Cavazza | 426/656 |
| 6,420,342 B1 * | 7/2002 | Hageman et al. | 514/23 |
| 6,521,591 B1 * | 2/2003 | Smeets et al. | 514/2 |
| 6,706,295 B2 * | 3/2004 | Mehansho et al. | 426/72 |

2001/0031729 A1    10/2001   Van Loon et al.

FOREIGN PATENT DOCUMENTS

| | | |
|---|---|---|
| DE | 297 09 313 | 9/1997 |
| EP | 1 112 693 | 7/2001 |
| FR | 2 758 243 | 7/1998 |
| JP | 9023825 | 1/1997 |
| WO | WO 01/58284 | 8/2001 |
| WO | WO 02/087562 | 11/2002 |

OTHER PUBLICATIONS

English abstract of FR 2 758 243.
English abstract of DE 297 09 313.
English abstract of JP 9023825.
Anello et al., "Chronic exposure to high leucine impairs glucose-induced insulin release by lowering the ATP-to-ADP ratio," *Am. J. Physiol. Endocrinol. Metab.*, 281:E1082-E1087 (2001).
Anthony et al., "Leucine Supplementation Enhances Skeletal Muscle Recovery in Rats Following Exercise," *J. Nutr.*, 129:1102-1106 (1999).
Anthony et al., "Orally Administered Leucine Stimulates protein Synthesis in Skeletal Muscle of Postabsorptive Rats in Association with Increased e1F4F Formation," *J. Nutr.*, 130:139-145 (2000).
Nagasawa et al., "Rapid suppression of protein degradation in skeletal muscle after oral feeding of leucine in rats," *J. Nutr. Biochem.*, 13:121-127 (2002).
Wolfe, "Effects of insulin on muscle tissue," *Current Opinion in Clinical Nutrition and Metabolic Care*, 3:67-71 (2000).

* cited by examiner

*Primary Examiner*—Sharon E. Kennedy
(74) *Attorney, Agent, or Firm*—Banner & Witcoff, Ltd

(57) ABSTRACT

The invention relates to a formulation in the form of a pharmaceutical composition, a food product, a feed product or a dietary supplement, comprising leucine and protein in specific amounts. Consumption of a formulation according to the invention has a very positive effect on the generation of muscle tissue and is therefore particularly useful for organisms wherein an anabolic response is desired.

24 Claims, No Drawings

STIMULATION OF IN VIVO PRODUCTION OF PROTEINS

The invention relates to a pharmaceutical composition, food or feed product or dietary supplement which stimulates the production of proteins in vivo. In particular, the invention relates to a formulation which induces generation of muscle tissue.

In the body of a mammal, such as man, production and degradation of proteins occurs continuously. The processes that are involved, are responsible for replacement of aged or damaged cells and tissues. Concurrently, these process are responsible for growth. The production and degradation of proteins are, particularly when viewed over a prolonged period of time, in balance. In a mature organism, the total protein mass is near constant.

Under certain circumstances, this balance is disturbed. Due to the effect of specific pathologies or their treatment, trauma (e.g. after extensive surgery), or during a period of poor nourishment, net catabolism may take place. This means that the amount of protein mass disappearing in degradation processes outweighs the amount of protein produced. In the degradation of certain tissues, in particular muscle tissue, amino acids may be released which are necessary for maintaining specific bodily functions that may be essential under the given circumstances. It is desired that such catabolic processes are stopped or at least slowed down as much as possible, or, even more preferably, prevented.

Much research has been done to design formulations that can be administered to organisms in catabolic state. These formulations are generally administered as food supplements in the phase of recovery, e.g. after surgery or undernourishment, and are intended to slow down or reverse catabolic processes. These formulations have to be distinguished from formulations used to provoke an anabolic response in healthy subjects.

Certain groups of people feel a need to generate a strong anabolic reaction in their bodies. Their aim is to achieve a larger Lean Body Mass (LBM). This wish is strong with sportsmen, in particular those performing power sports, but also with people who consider a heavy muscular physique to be an aesthetic virtue. Generally, formulations intended for provoking an anabolic response in these people are designed to interact with the body's mechanistic functions resulting from (heavy) physical exercise.

There are many commercially available products that aim to induce anabolic reactions.

The product Megawhey™ (available from GNC) contains per daily dose of 63 grams: 40 grams of whey, 5 grams of L-glutamine, 0.7 grams of isoleucine, 1.5 grams of leucine, 0.8 grams of L-valine, 4 grams of lipids, and 4 grams of carbohydrates. The remaining 7 grams of each dose is made up of calcium, potassium and sodium salts, citric acid, Xanthan gum, taste enhancers and water. The total amount of leucine in the product corresponds to 6.2 grams per dose, while the total amount of amino acids corresponds to 55.2 grams per dose. Thus, the amount of leucine is less than 11.2% of the total amount of amino acids in each dose.

The international patent application 01/58284 discloses a pharmaceutical composition for enhancing anabolic reactions. The composition is based on three components: an initiator (such as a specific growth factor), a substrate (such as a protein or mixture of amino acids), and a facilitator (e.g. creatine or a vitamin). The amount of L-leucine in the composition per daily dose is between 3 and 20 grams. The ratio between the amount of L-leucine and other branched amino acids is between 0.5 and 3, and preferably between 0.46 and 0.8. Example 1 shows a composition of 30 grams consisting of 9.4 grams of protein equivalents, including 2 grams of L-leucine and 5 grams of soy protein, which provides 0.4 grams of L-leucine in 5.9 grams of amino acids, and further 2 grams of creatine, 13.6 grams of glucose syrup and 2 milligrams of vitamin B6, leading to a ratio of leucine to amino acids of 0.233 and a ratio of leucine to the total weight of the formula of 0.081.

U.S. Pat. No. 5,817,329 relates to a diet supplement for athletes, which may have one of three different forms. One of these comprises 21.7 grams of leucine per 100 grams of product, and 28.6 grams of leucine per 100 grams of amino acids. None of the disclosed supplements, however, contains any protein or protein hydrolysate.

U.S. Pat. No. 5,639,731 discloses a beverage which is meant to improve mental fitness during heavy physical exercise. The preparation contains 2 to 40 grams per liter of branched amino acids, 50 to 750 grams per liter of oligosaccharides and has a specific pH and osmolarity. The only amino acids that may be present in the preparation are isoleucine, leucine and valine. To mask the bitter taste of these amino acids, the preparation contains relatively large amounts of sweeteners and taste enhancers.

Many of the known formulations intended to provoke anabolic reactions, not only have high carbohydrate contents, but also very high protein and/or amino acid contents. Free amino acids however, in particular branched amino acids, have an intense bitter taste. A high protein content is also disadvantageous from a cost perspective. Due to the large amounts of the formulation that is consumed by each user, the user's appetite may be significantly reduced by this consumption. This could result in a reduced intake of other important foodstuffs.

It is desired that a formulation is provided that selectively provokes an anabolic response without potential disadvantages with regard to satiety or practical discomfort during exercise. It is furthermore desired that such a formulation has an acceptable taste.

Anthony et al. have described in J. Nutr. 130, 139-145, 2000 that administration of L-leucine normalized protein synthesis in undernourished rats. The same group reported in J. Nutr. 129, 1102-1106, 1999 that administration of L-leucine to food-deprived rats immediately after heavy physical exercise resulted in a protein biosynthesis comparable to rats that have just been fed. In both publications, the formulation was administered to the rats after exercise and contained, in addition to L-leucine, considerable amounts of carbohydrates and no protein.

Based on these reports, it was expected that L-leucine by itself could be used as dietary supplement to provoke an anabolic reaction in undernourished, i.e. catabolic, subjects. However, experimentally it was found, as shown in the appended examples, that administration of L-leucine alone does not induce the desired response in protein production.

There is, in fact, some suggestion in the literature (Anello et al., Am. J. Physiol. Endocrinol. Metab., 281, E1082-E1087, 2001) that exposure to high amounts of leucine impairs insulin release and thereby has an adverse effect on human muscle protein synthesis. The effects of insulin on muscle tissue have, inter alia, been discussed by Wolfe, Current Opinion in Clinical Nutrition and Metabolic Care, 3, 67-71, 2000.

Other studies seem to suggest that significant amounts of carbohydrates must be co-administered with leucine to provoke an anabolic response. U.S. patent application 2001/0031,729 discloses a composition comprising carbohydrate and peptide material for use as an energy supplement after or during exercise. The experimental study that forms the basis for the postulation of the composition focuses solely on blood insulin response. Also, Nagasawa et al.'s statement (Journal of Nutritional Biochemistry, 13, 121-127, 2002) that leucine may be a regulating factor of myofibrillar protein degradation after refeeding of a protein diet is based on an experiment in which leucine was administered together with large amounts of carbohydrates and no other proteinaceous material or free amino acids to food-deprived rats.

In accordance with the invention, it has been found that a specific combination of L-leucine and proteins has a significant effect on the in vivo production of proteins, and thereby also on the generation of muscle and skin tissue. This effect has, surprisingly, been found to be particularly apparent when a formulation according to the invention is consumed just before heavy physical exercise is started.

In a first embodiment, the invention provides a formulation in the form of a pharmaceutical composition, a food product or a dietary supplement comprising leucine and proteins, wherein the total amount of leucine is at least 3 grams and the weight ratio of leucine to other amino acids is between 0.2 and 0.4, per serving of 25 grams for a human subject of 80 kilograms. This means that the dosage of leucine is at least 0.037 grams, and preferably more than 0.04 grams of leucine per kilogram of body weight per serving. More specifically, the invention relates to a formulation comprising L-leucine and protein, wherein the total amount of leucine is at least 10 wt. % based on the total dry weight of the formulation and the weight ratio of leucine to other amino acids is between 0.2 and 0.4.

Consumption of a formulation according to the invention has a very positive effect on the build-up of muscle tissue. It is therefore highly useful for organisms, particularly mammals, wherein an increase in Lean Body Mass is desired, such as athletes. In many cases the anabolic response to a formulation according to the invention is much higher than that to the known formulations for this purpose.

As mentioned above, a formulation according to the invention is particularly advantageous when used shortly before physical exercise. Without wishing to be bound by theory, it is believed that the components included in the formulation will influence the physical phenomena occurring in the human body during physical exercise. Examples of these phenomena are a large consumption of glucose, degradation of glycogen, production of metabolic degradation products like lactic acid, large consumption of water, increase in body temperature, damage to tissues apart from the "normal" wearing out of tissue, and the like. Simultaneous availability of essential amino acids and leucine in high amounts to muscle cells has a stimulatory effect on the anabolic processes, particularly protein synthesis during the recovery phase. The balance between anabolic and catabolic processes will shift more towards the anabolic state. Similarly, a formulation according to the invention is also of advantage when administered shortly before a subject is exposed to catabolic or catabolic inducing conditions, such as surgery. In such a case, catabolic processes in the body may be, at least partially, prevented.

Of particular advantage is that a formulation according to the invention may contain relatively low amounts of proteinaceous matter compared to conventional commercially available preparations, while provoking a strong anabolic reaction. This ensures improved palatability and maintenance of appetite. Because of this, the formulation can suitably be combined with a normal diet. The relatively small volume that needs to be consumed per serving of a formulation according to the invention (about 25 grams per serving compared to more than 50 grams per serving for conventional formulas) also allows an excellent compliance when used shortly before exercise.

The leucine used in a formulation according to the invention is preferably the L-isomer. However, the formulation may also comprise the D-isomer instead of or in combination with the L-isomer, for instance when leucine is present in the form of a racemate. The leucine can be included in the form of a di-, tri- or oligopeptide, but also when part of a protein or protein hydrolysate as discussed below. It is furthermore possible to use 2-oxo-isocaproic acid or a salt or ester thereof as this will provide leucine in vivo. It is preferred, however, that at least part of the leucine present in a formulation according to the invention is added in the form of the free amino acid as the L-isomer. It is to be noted that when leucine is present in an alternative form as discussed in this paragraph, the dosage in the formulation is based on free leucine. The amounts for such alternative forms accordingly need to be adjusted to comply with said dosage.

A formulation according to the invention comprises at least 2.5 grams, preferably 3 to 8 grams, more preferably at least 3.2 grams of leucine per serving of 25 grams for a human being of 80 kilograms. Preferably, a formulation according to the invention comprises 10-80 wt. %, more preferably 12-60 wt. % leucine, calculated on dry substance.

It is further desired that the amount of leucine in a formulation according to the invention is large when compared to the amount of other branched amino acids. Branched amino acids are, apart from leucine, valine and isoleucine. Preferably, the weight ratio of the amount of leucine to the total amount of branched amino acids, including leucine, per daily dose higher than 0.48. More preferably, the weight ratio of leucine to the sum of valine and isoleucine per daily dose is between 0.88 and 20, even more preferably between 1.1 and 10.

It is preferred that a formulation according to the invention comprises in total at least 5 grams of essential amino acids, in particular methionine and lysine. Of course, these amino acids may also (partly) be present as part of larger protein products such as those discussed below.

Although a formulation according to the invention may comprise digestible carbohydrate material, it is preferred that the amount thereof is relatively small. In particular, mono- and disaccharides, and especially lactose, fructose and sucrose, are present in very low amounts, or virtually absent. The amount of digestible mono- and disaccharides and preferably of all digestible carbohydrates should not exceed that of 20 wt. %, based on the total weight of the formulation, and is preferably below 10 wt. %, more preferably below 5 wt. %.

In a preferred embodiment, a formulation according to the invention further comprises one or more of the vitamins folic acid, vitamin B6, vitamin B1, vitamin B2, biotin, lipoic acid, and vitamin B12. Per serving of 25 grams for a subject of 80 kilograms, preferred ranges for the amounts of these components are 0.2-1.0 mg folic acid, 0.25-1.0 mg vitamin B6, 0.5-10 µg vitamin B12 preferably in the form of hydroxy cobalamine, 0.25-1.0 mg vitamin B1, 0.25-1.0 mg vitamin B2, and 0.25-10 mg biotin. Hydroxymethyl butyrate, creatine or an equivalent thereof (e.g. a salt, such as guanidino acetate for creatine) or small amounts of nutritional, indigestible fibres may also be included. Typical examples of fibres are indigestible carbohydrates such as poly- or oligosaccharides, e.g. soluble mannans, xylans, arabans, fructans, and the like, resistant starches or lignans. Preferably, the fibres used are soluble in water at ambient temperature.

As mentioned, in addition to leucine, a formulation according to the invention comprises proteinaceous matter. This proteinaceous matter will generally have the form of an intact protein of natural, preferably of animal origin. Preferably, the proteinaceous matter in a formulation according to the invention comprises more than 90 wt. % of intact proteins or peptides. Suitable examples include whey protein isolates, whey protein concentrates, caseins as well as salt forms thereof (caseinates), specific whey proteins such as β-lactoglobulin, α-lactalbumin, lactoferrin, immunoglobulins and the like, egg proteins, in particular chicken egg proteins with low avidin content, and combinations thereof. Particularly preferred are whey and whey proteins. It is to be noted that hydrolysates of these proteins can also be used, however, the total amount of amino acids and peptides is preferably not higher than 50% and more preferably not higher than 30% of the total amount of proteinaceous matter present. Of the total weight of amino acids in the formulation as determined after complete hydrolysis of the proteinaceous matter (so including that of the protein, protein hydrolysate and other proteinaceous matter, if present), between 20 and 40%, preferably between 25 and 37%, even more preferably between 28 and 35%, is leucine. It should be noted, however, that preferably the total amount of proteinaceous material, including leucine, in a formulation according to the invention is at least 25%, more preferably at least 50%, and even more preferably at least 75%. Further preferred is an embodiment wherein the protein is present in such an amount as to give a total amount of amino acids in the range of 40 to 80 wt. %, preferably 60 to 75 wt. %, calculated on dry substance.

As mentioned, a formulation according to the invention may have the form of a pharmaceutical composition, a food product, or a dietary supplement. Alternatively, a formulation according to the invention can be used in the manufacture of various types of products, such as food products (bars and the like).

A pharmaceutical composition may have the form of a beverage or a powder. In practice, the composition will be intended for oral administration. A food product may have different forms. Possibilities are products having a relatively high moisture content (50-90 wt. %) such as a pudding-like product (emulsions having a high solids content) and the like. It is, however, also possible to prepare a food product provoking an anabolic response having a relatively low moisture content (10-50 wt. %), e.g. in the form of snacks (sweet or salty/herbal flavoured). When a formulation according to the invention has the form of a dietary supplement it will usually have the form of a bar, a beverage or a powder. It is to be noted that the overall composition of the formulation, in particular the carbohydrate content, is not to be substantially affected by the preparation of these administration forms.

It is one of the advantages of a formulation according to the invention that it allows the manufacture of a food bar comprising a high protein content without the normally associated disadvantage of food bars having a high protein content of its hardness and toughness. Accordingly, the invention also provides a food bar comprising a protein formulation as discussed above and other suitable ingredients, which has an excellent mouthfeel and chewability. It is not too brittle or tough, but nevertheless sufficiently adherent. In order to prepare a food bar according to the invention about 20-40 wt. % of a protein-dominant formulation as discussed above is combined with about 20-40 wt. % of a carbohydrate fraction, and 2-10 wt. % of a lipid fraction, and optionally other conventional food bar ingredients.

It has been found that the effect of consumption or administration of a formulation according to the invention is particularly high when it is consumed shortly prior to the moment at which a strong production of muscle tissue is desired or needed. Examples of such moments include immediately preceding heavy physical exercise, such as a sports performance, but also just before undergoing surgery. Patients recovering from surgery are often restricted in their food intake, both in amount and in kind. In such a situation, a formulation according to the invention may prevent that the patient loses large amounts of muscular mass.

It is preferred that the formulation is consumed or administered in a period of up to 2 hours, preferably between 1 hour and immediately before the moment at which an anabolic response is desired. It is observed, however, that an optimal consumption/administration protocol can best be devised with a view to a specific physical exertion, for instance in the context of a recovery or training program. It will be understood that a formulation according to the invention can also be formulated to have controlled or delayed release of leucine, other amino acids as discussed above, and protein.

It has further been found that a formulation according to the invention has a positive effect on the rate of (re) generation of skin tissue. Thus, the formulation can advantageously be used for patients recovering from burns.

The invention further provides a means to provide an effective product that has excellent organoleptic properties.

The invention will now be elucidated by the following, non-restrictive examples.

EXAMPLE 1

A powder containing per 100 grams dry substance:
80 grams low fat milk powder (provides about 28 grams of protein, 33 grams of amino acids and 2.8 grams of leucine)
10 grams L-leucine
0.5 grams lysine
0.5 grams methionine
1 gram aspartate powder
1 gram vanilla flavour
1 gram citric acid
3.5 grams mineral pre-mix (providing 320 milligrams of sodium, 700 milligrams of potassium, 500 milligrams of chloride, 150 milligrams of calcium, 150 milligrams of phosphorous, 80 milligrams of magnesium, 5 milligrams of zinc, and 1 milligram of copper)
1 gram Xanthan gum
1.5 grams vitamin pre-mix (containing 1 mg folic acid, 20 μg cyanocobalamine, 6 mg pyridoxamine, 8 mg thiamine HCl, 8 mg riboflavine, and 1 mg biotin)

was prepared. Sachets were filled with 25 g powder, which can be dissolved in 200 ml drink, like water or other suitable liquid (tea) to provide one serving.

EXAMPLE 2

A powder was prepared of 22.0 grams whey protein concentrate (which provides 17.6 grams whey protein and 20.8 grams amino acids) and 4.4 grams of L-leucine.

EXAMPLE 3

A powder was prepared of 17 grams whey protein isolate (which provides 16.1 grams protein or 19 grams amino acids), 4.4 grams L-leucine and 200 milligrams caffeine and 100 milligrams of an aqueous extract of Schisandra.

EXAMPLE 4

A powder was prepared of 17 grams whey protein isolate hydrolysate, 4.4 grams L-leucine, 5 grams creatine, 2.6 grams citrate and 2.7 grams sodium phosphate.

EXAMPLE 5

A powder was prepared of 17 grams whey protein isolate, 4.4 grams L-leucine, 50 milligrams caffeine, 1 gram creatine monohydrate, 1 gram guanidino acetate, 1.0 gram serine, 0.2 milligrams of folic acid monoglutamate, 3 micrograms of cyanocobalamine, 0.85 milligrams of pyridoxin and 40 milligrams of ascorbic acid.

EXAMPLE 6

A food bar was prepared by combining per bar:
20 grams whey protein concentrate (80% protein)
5 grams L-leucine
5 grams glycerol
2 grams maltodextrin syrup
20 grams carbohydrate DE 19
5 grams rice flour
2 grams soy lecithin
2 grams cacao butter
2 grams inulin
2 grams cacao powder
3 grams oats fiber
1 grams vanilla flavour premix The protein composition is characterized by a leucine content of 32.8% related to the proteinaceous matter, Leu/BCAA=0.76, and Leu/(Val+Ile)=3.1.

EXAMPLE 7

Four groups of anaesthetized rats were given an amino acid composition. The same total amount of amino acids was given to each group by intravenous infusion. A fifth group was added to the study as a control group. The first group was given a balanced mixture of amino acids, commercially available under the trade name Travasol. This mixture contains less than 5% leucine. The second group was given 75% of Travasol and 25% of leucine. The third group was given 65% of Travasol and 35% of leucine, and the fourth group was given only leucine. The in fractional synthetic rate of mixed muscle protein synthesis (FSR (%/h)) was measured as described by Ferrando et al., Am. J. Physiol., 275, E864-E871, 1998, the contents of which are incorporated herein by reference. The results are summarized in the following Table:

| Group | FSR (%/h) |
| --- | --- |
| Travasol (7 rats) | 0.0867 ± 0.0253 |
| Travasol + 25% leucine (5 rats) | 0.1175 ± 0.0259 |
| Travasol + 35% leucine (5 rats) | 0.1258 ± 0.0334 |
| Leucine alone (5 rats) | 0.0767 ± 0.0204 |
| Control (6 rats) | 0.085 ± 0.0253 |

It is clear from these results that a relatively large amount of leucine with some other amino acids was the most effective.

What is claimed:

1. A composition comprising leucine and proteinaceous matter, wherein leucine is present in an amount of at least about 10 wt. % based on a total dry weight of the composition, in a weight ratio of between about 0.2 and 0.4 leucine to other amino acids present in the proteinaceous matter, and in a weight ratio of greater than about 0.48 leucine to a total amount of branched amino acids.

2. The composition of claim 1, wherein leucine is present in an amount of about 12 to 80 wt. % based on the total dry weight of the composition.

3. The composition of claim 1, wherein leucine is present in an amount of about 20 to 60 wt. % based on the total dry weight of the composition.

4. The composition of claim 1, wherein leucine comprises L-leucine.

5. The composition of claim 1, wherein leucine comprises free leucine.

6. The composition of claim 1, wherein leucine is present in a weight ratio of between about 0.88 and 20 leucine to a sum of valine and isoleucine.

7. The composition of claim 1, wherein leucine is present in a weight ratio of between about 1.1 and 10 leucine to a sum of valine and isoleucine.

8. The composition of claim 1 in a daily dosage amount, wherein leucine is present in a weight ratio of between about 0.29 and 0.35 leucine to other amino acids.

9. The composition of claim 1 in a dosage unit, wherein at least about 0.037 grams leucine is present per kilogram bodyweight per dosage unit.

10. The composition of claim 1 in a dosage unit, wherein at least 0.04 grams leucine is present per kilogram bodyweight per dosage unit.

11. The composition of claim 1, wherein the proteinaceous matter comprises at least about 90 wt. % intact proteins and/or peptides.

12. The composition of claim 1, wherein the proteinaceous matter is present in an amount such that the composition comprises about 40 to 80 wt. % amino acids, based on the total dry weight of the composition.

13. The composition of claim 1, wherein the proteinaceous matter is present in such an amount such that the composition comprises about 60 to 75 wt. % amino acids, based on the total dry weight of the composition.

14. The composition of claim 1 further comprising at least about 5 grams of essential amino acids.

15. The composition of claim 14 comprising synthetic L-lysine and/or synthetic L-methionine.

16. The composition of claim 1 further comprising one or more vitamins selected from the group consisting of folic acid, vitamin B6, vitamin B 1, vitamin B2, biotin, lipoic acid, and vitamin B12.

17. The composition of claim 1 further comprising mono- and disaccharides, wherein the mono- and disaccharides are present in an amount of less than about 20 wt. %, based on the total dry weight of the composition.

18. The composition of claim 1 further comprising mono- and disaccharides, wherein the mono- and disaccharides are present in an amount of less than about 10 wt. %, based on the total dry weight of the composition.

19. The composition of claim 1 further comprising mono- and disaccharides, wherein the mono- and disaccharides are present in an amount of less than about 5 wt. %, based on the total dry weight of the composition.

20. The composition of claim 1, wherein the composition is in a form selected from the group consisting of a pharmaceutical composition, a food product, and a dietary supplement.

21. A food bar comprising:
   the composition of claim 1 present in an amount of about 20-40 wt. % of the food bar;
   a carbohydrate present in an amount of about 20-40 wt. % of the food bar; and
   a lipid present in an amount of about 2-10 wt. % of the food bar.

22. The food bar of claim 21 further comprising conventional food bar ingredients.

23. A composition comprising leucine and proteinaceous matter, wherein leucine is present in an amount of at least about 10 wt. % based on a total dry weight of the composition, wherein leucine is present in a weight ratio of between about 0.2 and 0.4 leucine to other amino acids present in the proteinaceous matter, wherein the leucine is present in a weight ratio of greater than about 0.48 leucine to a total amount of branched amino acids, and wherein a total amount of amino acids and peptides is 50% or less than the total amount of the proteinaceous matter.

24. A composition comprising leucine and proteinaceous matter, wherein leucine is present in an amount of at least about 10 wt. % based on a total dry weight of the composition, wherein leucine is present in a weight ratio of between about 0.2 and 0.4 leucine to other amino acids present in the proteinaceous matter, wherein the leucine is present in a weight ratio of greater than about 0.48 leucine to a total amount of branched amino acids, and wherein a total amount of amino acids and peptides is 30% or less than the total amount of the proteinaceous matter.

* * * * *